(12) United States Patent
Abousleiman et al.

(10) Patent No.: US 7,650,795 B2
(45) Date of Patent: Jan. 26, 2010

(54) TEST CELL FOR APPLYING A SHEAR STRESS TO A TEST SPECIMEN

(75) Inventors: Younane Abousleiman, Norman, OK (US); John Brumley, Duncan, OK (US); Vinh Ngyuen, Norman, OK (US); Son K. Hoang, Norman, OK (US); Ashraf Al-Tahini, Dhahran (SA)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 12/045,423

(22) Filed: Mar. 10, 2008

(65) Prior Publication Data
US 2008/0216584 A1    Sep. 11, 2008

Related U.S. Application Data

(60) Provisional application No. 60/906,054, filed on Mar. 9, 2007.

(51) Int. Cl.
*G01N 3/24* (2006.01)

(52) U.S. Cl. ............................ 73/841; 73/760
(58) Field of Classification Search ............ 73/760–860
See application file for complete search history.

(56) References Cited

U.S. PATENT DOCUMENTS

| | | | | |
|---|---|---|---|---|
| 3,673,862 | A * | 7/1972 | Di Crispino et al. | 73/840 |
| 4,445,387 | A * | 5/1984 | Hall et al. | 73/845 |
| 4,567,774 | A * | 2/1986 | Manahan et al. | 73/826 |
| 4,579,003 | A | 4/1986 | Riley | |
| 4,854,175 | A | 8/1989 | Budhu | |
| 5,025,668 | A | 6/1991 | Sarda et al. | |
| 5,092,179 | A * | 3/1992 | Ferguson | 73/790 |
| 5,345,819 | A | 9/1994 | Dearing, Jr. | |
| 5,379,645 | A | 1/1995 | Smart | |
| 6,003,382 | A | 12/1999 | Puri et al. | |
| 6,539,809 | B1 * | 4/2003 | Weiss et al. | 73/825 |
| 2004/0074302 | A1 | 4/2004 | Matsiev et al. | |

OTHER PUBLICATIONS

International Search Report of co-pending PCT Application No. PCT/US08/56408, dated Jun. 30, 2008, 2 pgs.
Written Opinion of the International Searching Authority of co-pending PCT Application No. PCT/US08/56408, dated Jun. 30, 2008, 5 pgs.

* cited by examiner

*Primary Examiner*—Max Noori
(74) *Attorney, Agent, or Firm*—Dunlap Codding, P.C.

(57) ABSTRACT

A test cell and method for stress testing a test specimen including a first platen and a second platen. Each platen having a loading surface, an inclined surface, and a longitudinal axis. The inclined surface being inclined relative to the longitudinal axis at an angle and the inclined surface having a specimen recess formed therein for receiving a portion of the test specimen such that when the inclined surface of the second platen is positioned in a face-to-face relationship with the inclined surface of the first platen, a shear stress is applied to the test specimen when an axial load is applied to the first and second platens. The platens further including fluid ports to subject the test specimen to fluid flow at various pressures and fluid chemistries and ultrasonic transducers to determine acoustic, compressional, and shear wave velocities and in multiple orientations.

22 Claims, 2 Drawing Sheets

TEST CELL FOR APPLYING A SHEAR STRESS TO A TEST SPECIMEN

CROSS-REFERENCE TO RELATED APPLICATIONS

This application claims benefit of U.S. Provisional Application No. 60/906,054, filed Mar. 9, 2007, which is incorporated herein by reference in its entirety.

BACKGROUND OF THE INVENTION

1. Field of the Invention

The present invention relates generally to an apparatus that allows characterization of material mechanical and physical properties, and more particularly, but not by way of limitation, to a test cell that is capable of applying a shear stress to a small test sample of material, such as rock, bone, and cartilage, and which incorporates the ability to determine acoustic compressional and shear wave velocities in multiple orientations while the sample is subjected to an axial load and to fluid flow at various pressures and various fluid chemistries.

2. Brief Description of Related Art

Knowing the effects of fluid exposure and the directional dependency of mechanical properties such as strength and elastic/poroelastic coefficients is crucial for well-bore stability analysis, hydraulic fracturing design, and many other field applications in the oil and gas industry. Conventional test cells for loading test specimens apply a generally uniform radial pressure or confining stress and an axial stress. A Hoek cell, for instance, applies axial stress on the two ends of a cylindrical specimen, while the radial stress is developed by pressurizing a hydraulic fluid such as oil, around the cylindrical surface of the specimen, in a test chamber in which the specimen is held. The radial stress is angularly uniform in that it is the same in all radial directions and the only variations possible in relation to differential stress loading are axial and radial (angularly uniform) relative to each other.

Test data from the field has shown that the radial stress, more usually referred to as the horizontal stress, is defined by two principal stresses and is asymmetrical. The horizontal stress applied by a Hoek cell is symmetrical and, as such, not suitable for certain testing, such as well break-out, shear wave splitting, and fracture propagation testing. In order that specimens may be tested with asymmetrical, horizontal stresses, it has been necessary to prepare cubes of test material which much more accurately reflect the principal stresses encountered in an actual three dimensional situation. Such cuboid samples are, however, more difficult and expensive to prepare and test. Furthermore, cuboid samples generally cannot be prepared from the cylindrical test specimens normally obtained by conventional coring techniques used for sample recovery, e.g., in the petroleum industry.

To this end, a need exists for a test cell and method capable of subjecting a test sample to different applied stress states, and fluid circulation for any desired time of exposure, while the dynamic elastic moduli can be simultaneously acquired and monitored applying a shear stress to a test sample while also applying an axial load as well. It is to such a test cell and method that the present invention is directed.

DETAILED DESCRIPTION OF EXEMPLARY EMBODIMENTS OF THE INVENTION

Figure 1:
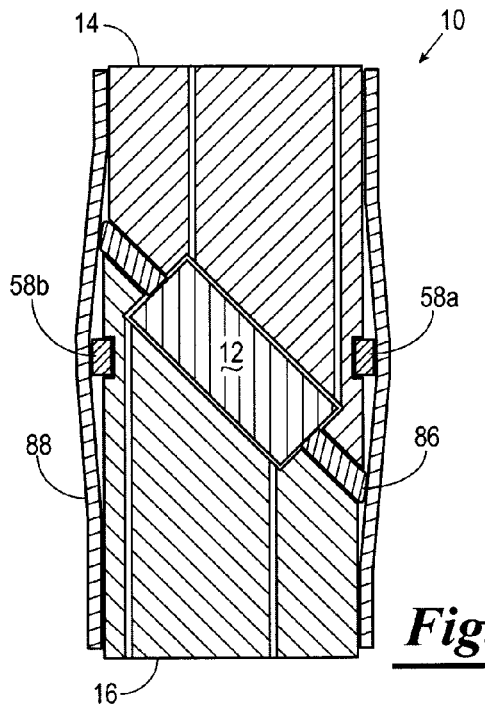
FIG. 1 is a sectional view of a test cell constructed in accordance with the present invention.
Figure 2:
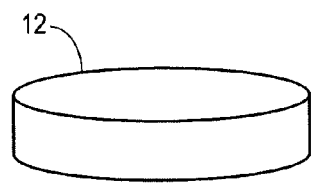
FIG. 2 is a perspective view of a cylindrical test specimen of rock.

Referring now to the drawings, and more particularly to FIG. 1, a test cell 10 constructed in accordance with the present invention is shown with a cylindrical test specimen 12 (FIG. 2) positioned therein. While the test cell 10 is shown in FIG. 1 containing a rock sample, it should be understood that the test cell 10 also has application on any porous or non-porous materials, in particular for bioengineering and biomechanics applications, such as bone characterization and bone weakening, cartilage elastic and plastic yields, while using the same set ups (in metal or in transparent composite material). One of the advantages of the test cell 10 is that it permits the testing of material samples that are significantly smaller in size than conventional rock and bone core samples.

Figure 3:
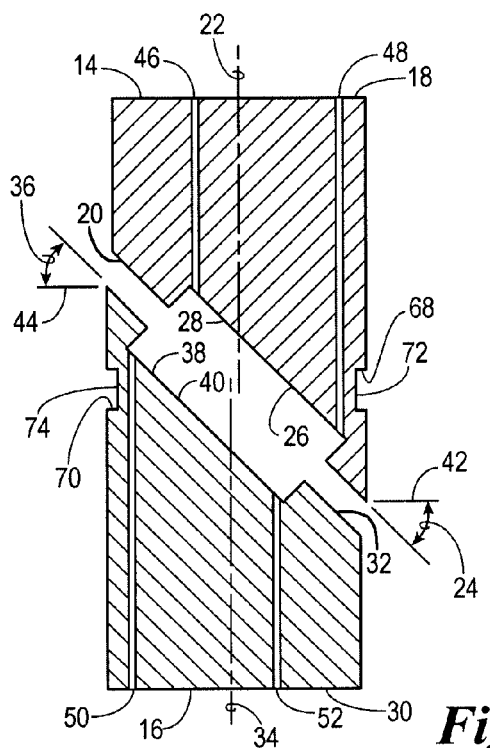
FIG. 3 is a cross-sectional view of a first platen and a second platen.

Referring now to FIGS. 1 and 3, the test cell 10 includes a first platen 14 and a second platen 16. The first platen 14 is shown to be positioned above the second platen 16 when the first and second platens 14 and 16 are arranged in a vertical orientation, as is common in conducting stress tests. However, it will be appreciated that the present invention is not limited to the orientation of the first and second platens 14 and 16. Each of the first and second platens 14 and 16, by way of example, may be a one inch diameter steel rod approximately two inches in overall length. However, it will be appreciated that the first and second platens 14 and 16 may be constructed in a variety of shapes and sizes and fabricated of a variety of materials. As best shown in FIG. 3, the first platen 14 has a loading surface 18 and an inclined surface 20. The loading surface 18 is preferably perpendicular to a longitudinal axis 22 of the first platen 14. The inclined surface 20 is inclined relative to the longitudinal axis 22 of the first platen 14 at an angle 24. The inclined surface 20 is provided with a specimen recess 26 for receiving a portion of the test specimen 12. The specimen recess 26 is preferably cylindrical in shape with a base 28 and oriented in a direction perpendicular to the inclined surface 20 with the base 28 parallel to the inclined surface 20.

Similarly, the second platen 16 has a loading surface 30 and an inclined surface 32. The loading surface 30 is preferably perpendicular to a longitudinal axis 34 of the second platen 16. The inclined surface 32 is inclined relative to the longitudinal axis 34 of the second platen 16 at an angle 36. The inclined surface 32 is provided with a specimen recess 38 for receiving another portion of the test specimen 12. The specimen recess 38 is preferably cylindrical in shape with a base 40 and oriented in a direction perpendicular to the inclined surface 32 and the base 40 is parallel to the inclined surface 32.

Referring again to FIG. 1, with the test specimen 12 positioned in the specimen recesses 28 and 40 of the first and second platens 14 and 16, respectively, such that the inclined surfaces 20 and 32 of the first and second platens 14 and 16 are in a face-to-face relationship, the inclined orientation of the specimen recesses 26 and 38 permit a shear stress to be applied to the test specimen 12 when an axial load is applied to the loading surfaces 18 and 30 of the first and second platens 14 and 16 in a manner to be described below. To this end, the specimen recesses 26 and 38 are each machined to a specified diameter and a specified depth for use with a test specimen of a specified size to prevent rotation of the test specimen 12 within the specimen recesses 26 and 38. Preferably, the test specimen 12 and the specimen recesses 26 and 38 are sized to cause the first platen 14 and the second platen 16 to be supported in a spaced apart relationship by the test specimen 12 when the test specimen 12 is seated in the specimen recesses 26 and 38 to permit the first and second platens 14 and 16 to move relative to one another when an axial load is applied. By way of example, with a test specimen having a diameter of 0.793 inches and a depth of 0.282 inches, the specimen recesses 26 and 38 are preferably machined to have a diameter of about 0.80 inches and a depth of about 0.90 inches. Also, it will be appreciated that while the angles 24 and 36 of the inclined surfaces 20 and 32 of the first and second platens 14 and 16 have been illustrated as being approximately 45 degrees relative to a plane 42 and a plane 44, respectively, extending perpendicular to the longitudinal axis 22 of the first platen 14 and the longitudinal axis 34 of the second platen 16, other inclination angles ranging from greater than 0 degrees to less than 90 degrees may be used provided stress and strain analysis is modified accordingly.

To enable the test specimen 12 to be subjected to fluid flow at various pressures and various fluid chemistries, each of the first platen 14 and the second platen 16 is provided with a pair of fluid ports. More specifically, the first platen 14 is provided with two fluid ports 46 and 48 which preferably intersect the base 28 of the specimen recess 26 at or near the perimeter of the base 28 at the highest and lowest points, respectively. Likewise, the second platen 16 is provided with two fluid ports 50 and 52 which preferably intersect the base 40 of the specimen recess 38 at the highest and lowest points, respectively. The fluid ports 46 and 50 may serve as injection ports, while the fluid ports 48 and 52 may serve as exit ports. The fluid ports 46-52 allow the circulation of a test fluid or series of test fluids across each face of the test specimen 12. This configuration allows three different modes of circulating fluid: (1) same upstream and downstream pressures can be used on both end of the specimen so that circulation fluid is flowed only on the two end surfaces; (2) different but uniform pressures can be used on the top and bottom surfaces, inducing fluid flow through the specimen; or (3) a combination of both flow types.

Fluid pore pressure and fluid flow can simultaneously be applied to the porous media, thus measuring strength and material parameters and variations of these when exposed to fluids with different chemistries, and while in contact with the fluids. A commercially available precision flow rate syringe pump with high pressure (10,000 psi) capability circulates the test fluid across the face of the test specimen 12. The test fluid circulated across the faces of the test specimen 12 is collected from the fluid discharge port(s) and may be analyzed using standard laboratory equipment to detect alterations in the chemical composition of the test fluid resulting from chemical reaction of the fluid with the test specimen 12. Determination of the mechanical properties of the test specimen 12 following contact with the test fluid allows an evaluation of the sensitivity of the sample material to various fluids or an evaluation of the effect of the duration of fluid exposure time if tests are performed with different fluid circulation times (for example, one hour, three hours, twenty-four hours).

Figure 6:
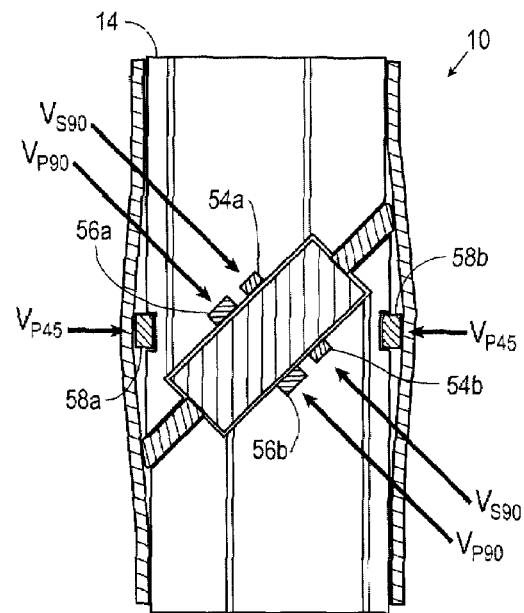
FIG. 6 is a schematic representation of the test cell.

Referring now to FIG. 6, shown is a schematic representation of the test cell 10 illustrating the first and second platens 14 and 16 functioning to house three pairs of ultrasonic transducers 54a and 54b, 56a and 56b, and 58a and 58b, to allow for measurements of P-wave velocity propagates in a direction perpendicular to the top and bottom of the test specimen 12, Vp90; S-wave velocity propagate in a direction perpendicular to the top and bottom of the test specimen 12, Vs90; and P-wave velocity propagate at angles 24 and 36, Vp45. These measured velocities can be used to obtain the full set of anisotropy stiffness coefficients and thus allow for monitoring of the changes of the elastic/poroelastic properties of the test specimen 12 when subjected to different applied stress states. The actual position of the ultrasonic transducers 54a and 54b, 56a and 56b, and 58a and 58b, will be described in detail below.

Figure 4:
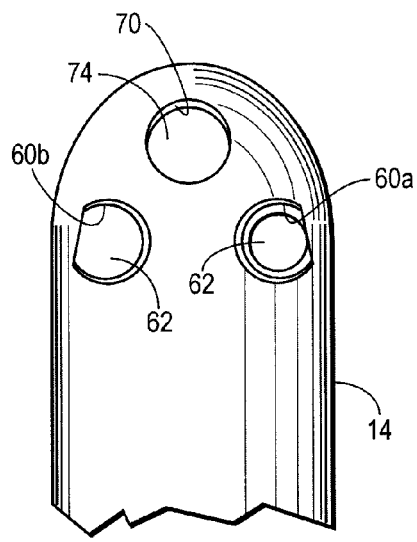
FIG. 4 is a perspective of a portion of the first platen.
Figure 5:
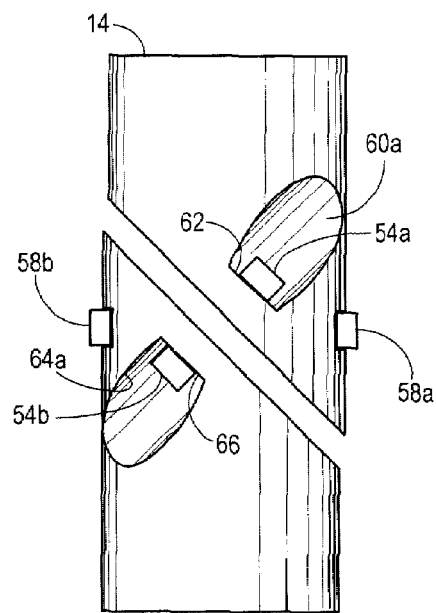
FIG. 5 is a is a side elevational view of the test cell.

As shown in FIG. 4, the first platen 14 has a pair of acoustic recesses 60a and 60b formed in an outer surface of the first platen 14. The acoustic recesses 60a and 60b each have a base 62 formed parallel to the base 28 of the specimen recess 26. As shown in FIG. 5, the second platen 16 has a pair of acoustic recesses 64a and 64b (only the recess 64a in view in FIG. 5) formed in an outer surface of the second platen 16. The acoustic recesses 64a and 64b of the second platen 16 also have a base 66 formed parallel to the base 40 of the specimen recess 38 of the second platen 16 and axially aligned with the acoustic recesses 60a and 60b of the first platen 14 when the test specimen 12 is seated in the specimen recesses 28 and 40 of the first and second platens 14 and 16. The acoustic recesses 60a, 60b and 64a, 64b are positioned such that a portion of the acoustic recesses 60a, 60b, and 64a, 64b is immediately behind the specimen recesses 28 and 40 and aligned along a diameter of the specimen recesses 26 and 38 perpendicular to a line through the fluid ports 46, 48 and 50, 52. In one embodiment, the acoustic recesses 60a, 60b and 64a, 64b are drilled to a depth to allow 0.2 inches of steel between the base of the specimen recess and the base of the acoustic recess.

Referring to FIGS. 3 and 4, the first platen 14 is further provided with a third acoustic recess 68, and the second platen 14 is provided with a third acoustic recess 70. The third acoustic recess 68 of the first platen has a base 72 formed parallel to the longitudinal axis 22 of the first platen 14, and the third acoustic recess 70 of the second platen 16 has a base 74 formed parallel to the longitudinal axis 34 of the second platen 16. In one embodiment, the third acoustic recesses 68 and 70 are machined to a maximum depth of about 0.050 inches on the outer surface of the first and second platens 14 and 16 aligned with the long point of the inclined surface 20 and 32, respectively, and positioned a distance back from the long point such that the third acoustic recesses 68 and 70 are positioned in an opposing relationship to each other and aligned with a center of the test specimen 12 when the test specimen 12 is seated in the specimen recesses 26 and 38 of the first and second platens 14 and 16.

The ultrasonic transducers 54a and 54b are mounted in the acoustic recesses 60a and 64a, the ultrasonic transducers 56a and 56b are mounted in the acoustic recesses 60b and 64b, and the ultrasonic transducers 58a and 58b are mounted in the acoustic recesses 68 and 70. In one embodiment, the ultrasonic transducers are preferably specific frequency piezoelectric crystals (600 kilohertz, 1 megahertz, or 2 megahertz) with a diameter of 0.25 inches. The ultrasonic transducers 54a and 54b preferably generate compression waves, the ultrasonic transducers 56a and 56b shear waves, and the ultrasonic transducers 58a and 58b compression waves.

The formation of a test cell stack 80 will now be described with reference to FIG. 7. Loading spacers 82 and 84 are positioned on the loading surfaces 18 and 30 of the first and second platens 14 and 16. The loading spacers 82 and 84 are preferably steel rods one inch in length and one inch in diameter which have two recesses (not shown) machined partially through the length thereof. One recess is positioned near the outer surface of the loading spacer. The second recess is positioned near the center of the loading spacer with a slot extending to the outer edge of the loading spacer. The midline of the recess matches the position of the fluid ports 46-52 of the first and second platens 14 and 16 to permit tubing 85 to be connected to the fluid ports 46-52.

A soft metallic acoustic coupling disc (not shown) with etched flow channels and fluid passage ports is positioned in the base of the specimen recesses 26 and 38 of both the first and second platens 14 and 16 to provide acoustic coupling between the platens 14 and 16, and the test specimen 12. The circumferential outer surface of the test specimen 12 preferably is lightly coated with lubricant, such as a petroleum jelly, to minimize friction during specimen installation. The test specimen 12 is positioned in the specimen recess 38 of the second platen 16 which, along with its corresponding loading spacer 84, is positioned on a V-block (not shown) and clamped in position using a clamping device typically provided with the V-block. The first platen 14 and its corresponding loading spacer 82 are positioned on an identical sized V-block and positioned such that the test specimen 12 will enter the specimen recess 26 of the first platen 14.

The first and second platens 14 and 16 are moved axially toward each other until the test specimen 12 is seated in the specimen recesses 26 and 38. A bar clamp (not shown) with one fixed clamp end and one adjustable clamp end is brought in contact with a loading surface of the loading spacers 82 and 84 and tightened to hold the composite sample stack in position and seat the test specimen 12 in the specimen recesses 26 and 38. Excess lubricant is removed from the edge of test specimen 12 exposed in the gap between the first and second platens 14 and 16. A thin strip of flexible rubber self-vulcanizing tape (not shown) is applied to the exposed surface of the test specimen 12 in the gap between the first and second platens 12 and 14. The gap between the first and second platens 14 and 16 is then filled with a pliable material 86, such as a commercially available hot melt glue or other suitable material, to permit the transmission of a confining pressure to the test specimen 12 while allowing relative movement between the first platen 14 and the second platen 16. After the pliable material 86 has solidified, the bar clamp is removed. A strip of flexible rubber self-vulcanizing tape (not shown) is wound around the outer surface of each of the first and second platens 14 and 16 near the inclined surfaces 20 and 32 and the loading surfaces 18 and 30 to create pressure sealing areas on the outer surface of the first and second platens 14 and 16.

A fluid impervious heat shrink tube 88 is positioned about the platens 14 and 16 and a soft temper lock wire (not shown) is wrapped around the heat shrink tube 88 at the positions of the self-vulcanizing tape and tightened to seal the heat shrink tube 88 against the tape. Another section of heat shrink tubing 88 is positioned around the assembled stack 80 including the loading spacers 82 and 84 and shrunk using a commercially available heat gun.

Electrical lead wires (not shown) with solid body end pins are pushed through the heat shrink tubing 88 to connect to the wiring connections on the ultrasonic transducers 54a, 54b, 56a, 56b, and 58a, 58b. The perforations in the heat shrink tube 88 are sealed with sealing material, such as hot melt glue and a small second layer of heat shrink tubing over the area of the perforations.

The assembled stack 80 is positioned in a test chamber 90 and held in position by plastic strips around tie-down loops on the base of the test chamber 90 and a fluid supply tubing is attached to the second platen 16. All tubing lines are connected inside the test chamber 90. All electrical leads are connected to appropriate electrical connections inside the test chamber 90 and tested for electrical short circuits. The test cell stack 80 is assembled.

Figure 7:
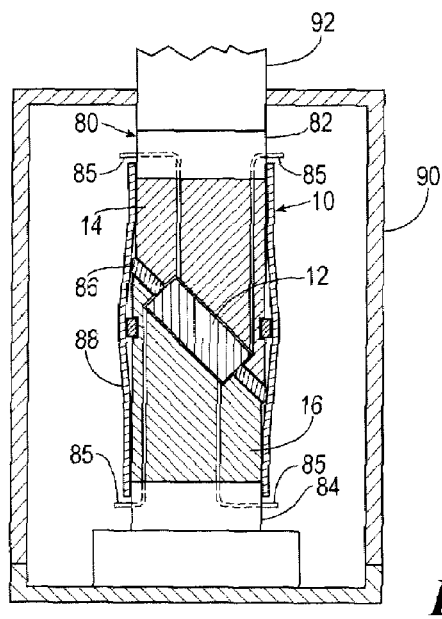
FIG. 7 is a cross-sectional view of the test cell shown disposed in a test chamber and connected to a load plunger.

As shown in FIG. 7, the test cell 10 is positioned on the base of the test chamber 90. A loading disc (not shown), may be positioned on the top of the loading spacer 82 to increase the contact area between the test cell 10 and a loading plunger 92 which passes through the top of the test chamber 90. The plunger 92 is positioned with a flat surface in contact with the test cell 10.

The entire test chamber 90 is installed in a loading frame (not shown) to apply force to the test cell 10. The test chamber 90 has the capability of being pressurized with fluid, such as water or oil, to provide a confining pressure to the test specimen 12 and heated to a specified temperature while in the loading frame to apply a hydrostatic force on the test cell 10 and thereby simulate in situ conditions. The loading force is increased by advancing the plunger 92 into the test chamber 90 at a constant rate of movement until the test specimen 12 experiences mechanical failure. Tests can be performed at various confining pressures within the operating limits of the test chamber 90 to characterize the mechanical properties of the test specimen 12.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed:

1. A test cell for stress testing a test specimen, comprising:
a first platen having a loading surface, an inclined surface, and a longitudinal axis extending from the loading surface to the inclined surface, the inclined surface of the first platen being inclined relative to a first plane perpendicular to the longitudinal axis of the first platen at an angle greater than zero degrees, the inclined surface having a specimen recess formed therein for receiving a portion of the test specimen, the specimen recess having a base formed parallel to the inclined surface; and
a second platen having a loading surface, an inclined surface, and a longitudinal axis extending from the loading surface to the inclined surface, the inclined surface of the second platen being inclined relative to a second plane perpendicular to the longitudinal axis of the second platen at an angle greater than zero degrees, the inclined surface having a specimen recess formed therein for receiving another portion of the test specimen, the specimen recess of the second platen having a base formed parallel to the inclined surface of the second platen, the second platen being substantially axially aligned with the first platen and the inclined surface of the second platen being positioned in a face-to-face, parallel relationship with the inclined surface of the first platen such that a shear stress is applied to the test specimen when the test specimen is positioned in the specimen recess of the first platen and the specimen recess of the second platen and a longitudinal axial load is applied to the first and second platens.

2. The test cell of claim 1 wherein the first platen has at least two fluid ports intersecting the base of the specimen recess of the first platen for selectively injecting a fluid into the specimen recess of the first platen.

3. The test cell of claim 2 wherein the second platen has at least two fluid ports intersecting the base of the specimen recess of the second platen for selectively injecting a fluid into the specimen recess of the second platen.

4. The test cell of claim 1 wherein the inclined surface of the first platen and the inclined surface of the second platen are supported in a spaced apart relationship by the test specimen when the test specimen is seated in the specimen recesses of the first and second platens.

5. The test cell of claim 4 further comprising:
a pliable material disposed between the inclined surface of the first platen and the inclined surface of the second platen so as to permit transmission of a confining pressure to a perimeter of the test specimen while allowing movement of the first and second platens relative to one another.

6. The test cell of claim 1 wherein the specimen recesses of the first platen and the second platen are cylindrical in shape.

7. The test cell of claim 1 wherein the first platen has a pair of acoustic recesses formed in an outer surface of the first platen, the acoustic recesses having a base formed parallel to the base of the specimen recess, and wherein the second platen has a pair of acoustic recesses formed in an outer surface of the second platen, the acoustic recesses of the second platen having a base formed parallel to the base of the specimen recess of the second platen and axially aligned with the acoustic recesses of the first platen when the test specimen is seated in the specimen recesses of the first and second platens, and wherein the test cell further comprises:
a first pair of ultrasonic transducers positioned in axially aligned acoustic recesses of the first and second platens; and
a second pair of ultrasonic transducers positioned in the other axially aligned acoustic recesses of the first and second platens.

8. The test cell of claim 7 wherein the first pair of ultrasonic transducers is capable of generating compression waves.

9. The test cell of claim 8 wherein the second pair of ultrasonic transducers is capable of generating shear waves.

10. The test cell of claim 7 wherein the first platen further comprises a third acoustic recess formed in the outer surface thereof, the third acoustic recess having a base formed parallel to the longitudinal axis of the first platen, wherein the second platen further comprises a third acoustic recess formed in the outer surface thereof, the third acoustic recess of the second platen having a base formed parallel to the longitudinal axis of the second platen, the third acoustic recesses of the first and second platens formed in an opposing relationship to each other and aligned with a center of the test specimen when the test specimen is seated in the specimen recesses of the first and second platens, and wherein the test cell further comprises:
a third pair of ultrasonic transducers positioned in the third acoustic recesses of the first and second platens.

11. The test cell of claim 10 wherein the third pair of ultrasonic transducers are capable of generating compression waves.

12. The test cell of claim 1 further comprising a flexible, fluid impervious sleeve disposed about the first and second platens when the test specimen is seated in the specimen recesses of the first and second platens.

13. A method of stress testing a test specimen, comprising:
positioning the test specimen in a test cell comprising:
a first platen having a loading surface, an inclined surface, and a longitudinal axis extending from the loading surface to the inclined surface, the inclined surface of the first platen being inclined relative to a first plane perpendicular to the longitudinal axis of the first platen at an angle greater than zero degrees, the inclined surface having a specimen recess formed therein for receiving a portion of the test specimen, the specimen recess having a base formed parallel to the inclined surface; and
a second platen having a loading surface, a inclined surface, and a longitudinal axis extending from the loading surface to the inclined surface, the inclined surface of the second platen being inclined relative to a second plane perpendicular to the longitudinal axis of the second platen at an angle greater than zero degrees, the inclined surface of the second platen having a specimen recess formed therein for receiving another portion of the test specimen, the specimen recess of the second platen having a base formed parallel to the inclined surface thereof, the second platen being substantially axially aligned with the first platen and the inclined surface of the second platen being positioned in a face-to-face, parallel relationship with the inclined surface of the first platen with the test specimen positioned in the specimen recess of the first platen and the specimen recess of the second platen; and
applying a longitudinal axial load to the first and second platens such that a shear stress is applied to the test specimen.

14. The method of claim 13 wherein the test specimen is cylindrical in shape and has a first planar end and a second planar end, and wherein the method further comprises the step of injecting a fluid into the specimen recess of the first platen so as to cause the fluid to flow over the first planar end of the test specimen and be discharged from the specimen recess.

15. The method of claim 14 further comprising the step of injecting a fluid into the specimen recess of the second platen so as to cause the fluid to flow over the second planar end of the test specimen and be discharged from the specimen recess.

16. The method of claim 13 further comprising the step of injecting a fluid into the specimen recess of one of the first and second platens so as to cause the fluid to flow through the test specimen.

17. The method of claim 13 further comprising the step of injecting a fluid into the specimen recess of the first and second platens so as to cause the test specimen to be immersed in the fluid.

18. The method of claim 13 wherein the inclined surface of the first platen and the inclined surface of the second platen are spaced apart, and wherein the method further comprises the step of applying a confining pressure to the test specimen.

19. The method of claim 13 further comprising the step of:
transmitting ultrasonic compression waves through the test specimen in a direction perpendicular to the bases of the specimen recesses of the first and second platens.

20. The method of claim 19 further comprising the step of:
transmitting ultrasonic shear waves through the test specimen in a direction perpendicular to the bases of the specimen recesses of the first and second platens.

21. The method of claim 20 further comprising the step of:
transmitting ultrasonic compression waves through the test specimen in a direction perpendicular to the longitudinal axis of the first and second platens.

22. The method of claim 13 further comprising the step of:
transmitting ultrasonic compression waves through the test specimen in a direction perpendicular to the longitudinal axis of the first and second platens.

* * * * *